US012558182B2

(12) United States Patent
Balter et al.

(10) Patent No.: US 12,558,182 B2
(45) Date of Patent: Feb. 24, 2026

(54) METHODS AND APPLICATIONS FOR FLIPPING AN INSTRUMENT IN A TELEOPERATED SURGICAL ROBOTIC SYSTEM

(71) Applicant: Covidien LP, Mansfield, MA (US)

(72) Inventors: Max L. Balter, Newton, MA (US); Burak Yilmaz, Upton, MA (US); William J. Peine, Ashland, MA (US)

(73) Assignee: Covidien LP, Mansfield, MA (US)

( * ) Notice: Subject to any disclaimer, the term of this patent is extended or adjusted under 35 U.S.C. 154(b) by 533 days.

(21) Appl. No.: 18/013,280

(22) PCT Filed: Jul. 13, 2021

(86) PCT No.: PCT/US2021/041379
§ 371 (c)(1),
(2) Date: Dec. 28, 2022

(87) PCT Pub. No.: WO2022/026168
PCT Pub. Date: Feb. 3, 2022

(65) Prior Publication Data
US 2023/0310108 A1 Oct. 5, 2023

Related U.S. Application Data

(60) Provisional application No. 63/056,760, filed on Jul. 27, 2020.

(51) Int. Cl.
*A61B 34/00* (2016.01)
*A61B 34/30* (2016.01)
(Continued)

(52) U.S. Cl.
CPC .............. *A61B 34/77* (2016.02); *A61B 34/25* (2016.02); *A61B 34/35* (2016.02); *A61B 34/74* (2016.02); *B25J 9/1689* (2013.01); *B25J 9/1697* (2013.01)

(58) Field of Classification Search
CPC ......... A61B 34/77; A61B 34/25; A61B 34/35; A61B 34/74; A61B 2090/034;
(Continued)

(56) References Cited

U.S. PATENT DOCUMENTS 6,491,701 B2 * 12/2002 Tierney .................. A61B 46/13
606/130
9,770,300 B2 * 9/2017 Kwon ........................ B25J 3/04
(Continued)

FOREIGN PATENT DOCUMENTS

WO      2017151850 A1      9/2017

OTHER PUBLICATIONS

International Search Report and Written Opinion of the International Searching Authority issued in corresponding application PCT/US2021/041379 mailed Nov. 16, 2021 (14 pages).

*Primary Examiner* — Jaime Figueroa
(74) *Attorney, Agent, or Firm* — Carter, DeLuca & Farrel

(57) ABSTRACT

According to one embodiment of the present disclosure, a surgical robotic system includes a robotic arm having an instrument drive unit and a surgical instrument rotatable by the instrument drive unit about an instrument axis. The system also includes a surgical console including at least one handle controller having a handle rotatable about a handle axis and configured to receive a user input for moving the surgical instrument. The system further includes a controller configured to receive the user input and to instruct the robotic arm to flip the surgical instrument in response to the user input, wherein the user input is an angle of rotation of the handle about the handle axis that is less than an angle of rotation of the surgical instrument of about 180°.

15 Claims, 6 Drawing Sheets

(51) Int. Cl.
    *A61B 34/35*       (2016.01)
    *B25J 9/16*        (2006.01)

(58) Field of Classification Search
    CPC ... A61B 2090/035; A61B 34/37; A61B 34/30;
                   B25J 9/1689; B25J 9/1697
    USPC ................. 700/245–264; 318/568.11–568.25
    See application file for complete search history.

(56) References Cited

U.S. PATENT DOCUMENTS

| | | | | |
|---|---|---|---|---|
| 10,413,374 | B2 * | 9/2019 | Chassot | A61B 18/1442 |
| 11,369,448 | B2 * | 6/2022 | Hassan | A61G 13/08 |
| 11,399,905 | B2 * | 8/2022 | Schuh | A61B 34/35 |
| 11,471,178 | B2 * | 10/2022 | Brasset | A61B 34/37 |
| 11,628,023 | B2 * | 4/2023 | Troxell | A61B 34/10 |
| | | | | 623/17.11 |
| 12,121,313 | B2 * | 10/2024 | Lim | G16H 20/40 |
| 12,167,897 | B2 * | 12/2024 | Lim | A61B 90/50 |
| 2003/0083673 | A1 * | 5/2003 | Tierney | H01H 36/0046 |
| | | | | 606/130 |
| 2010/0228264 | A1 * | 9/2010 | Robinson | A61B 18/1206 |
| | | | | 606/130 |
| 2011/0022229 | A1 * | 1/2011 | Jang | B25J 13/02 |
| | | | | 901/41 |
| 2014/0241577 | A1 * | 8/2014 | Kwak | G06T 7/277 |
| | | | | 382/103 |
| 2015/0066051 | A1 * | 3/2015 | Kwon | A61B 34/76 |
| | | | | 606/130 |
| 2018/0310999 | A1 | 11/2018 | Peine | |
| 2019/0239972 | A1 * | 8/2019 | Chassot | A61B 34/77 |
| 2019/0328470 | A1 | 10/2019 | Tojo et al. | |
| 2019/0328473 | A1 | 10/2019 | Chassot et al. | |
| 2019/0374297 | A1 * | 12/2019 | Wallace | A61B 34/71 |
| 2020/0000533 | A1 * | 1/2020 | Schuh | A61B 34/71 |
| 2020/0093554 | A1 * | 3/2020 | Schuh | A61B 17/00234 |
| 2020/0100853 | A1 * | 4/2020 | Ho | A61B 34/71 |
| 2020/0179068 | A1 | 6/2020 | Peine et al. | |
| 2020/0305983 | A1 * | 10/2020 | Yampolsky | A61G 13/02 |
| 2020/0315723 | A1 * | 10/2020 | Hassan | A61B 1/307 |
| 2020/0405420 | A1 * | 12/2020 | Purohit | B25J 9/02 |
| 2021/0007811 | A1 * | 1/2021 | Troxell | A61B 17/1671 |
| 2021/0038241 | A1 * | 2/2021 | Brasset | A61B 34/37 |
| 2021/0244489 | A1 * | 8/2021 | Lim | B25J 18/007 |
| 2022/0047345 | A1 * | 2/2022 | Choi | B25J 19/06 |
| 2022/0054209 | A1 * | 2/2022 | Lim | G16H 40/67 |

\* cited by examiner

METHODS AND APPLICATIONS FOR FLIPPING AN INSTRUMENT IN A TELEOPERATED SURGICAL ROBOTIC SYSTEM

CROSS REFERENCE TO RELATED APPLICATIONS

The present application is a U.S. National Stage Application filed under 35 U.S.C. § 371(a) of PCT/US2021/041379, filed on Jul. 13, 2021, which claims the benefit of and priority to U.S. Provisional Patent Application No. 63/056,760, filed Jul. 27, 2020. The entire disclosures of the foregoing applications are incorporated by reference herein.

BACKGROUND

1. Technical Field

The present disclosure generally relates to a surgical robotic system having one or more modular arm carts each of which supports a robotic arm and a surgical console for controlling the carts and their respective arms. More particularly, the present disclosure is directed to a system and method for flipping an instrument held by the robotic arm by rotating the instrument about a longitudinal axis about 180° using a flip command input through a handle controller of the surgical console.

2. Background of Related Art

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. The surgical console includes controllers that provide haptic feedback to the clinician using the surgical console. In certain situations, particularly those arising during use of asymmetrical instruments, such as curve blade instruments, there is a need for a surgical robotic system that is capable of flipping the instrument without flipping a handle controller in a mirror movement, i.e., 180° about a longitudinal axis, since that requires cumbersome double-clutching movement.

SUMMARY

The present disclosure provides a surgical robotic system allowing for teleoperation of instrument movable via robotic arm coupled to a movable cart. The robotic arm and the instrument are controlled through a surgical console having two handle controllers, each of which is paired to one instrument. The instrument mirrors movement of the handle controllers. However, there are several cases where the clinician may need to flip an end-effector. As used herein, flipping an instrument denotes changing orientation of the instrument by applying a 180° offset to the instrument about a longitudinal axis, i.e., roll direction. When using asymmetric end effectors, such as curved-tip instruments, the curvature of the jaws needs to align with the cutting, dissection, or grasping direction. It is also useful for cautery tools to apply energy with the top or curved part of the jaws. In these instances, these curved tipped instruments may realign in the opposite direction with the curvature of the jaw facing outward. Triggering an instrument flip on the surgeon console, resolves this issue by flipping the end effector.

The present disclosure also enhances the range-of-motion in the axial, roll direction of symmetric-tip instruments, which occurs due to mechanical hard-stops on the roll-axis when targeting anatomy during challenging procedure workspace setups. The present disclosure provides for a unique control scheme using handle controllers of the surgical console to initiate instrument flip when the user clutches the handle controller on the surgeon console by pressing a foot pedal and rotates the handle controller about a scaled joint angle by about +/−135°. The rotation scaling factor may correspond to the value selected by the user on a surgeon interactive display of the surgical console or selected automatically by the surgical console after selecting a threshold angle.

Specifically, the instrument flip algorithm according to the present disclosure allows surgeons to use curved-tip instruments, such as scissors, in the correct orientation. If a curved-tip instrument was attached to a robot arm in a misaligned state without a method of easily flipping the instrument, it would significantly impede the effectiveness of the curved-tip instrument. Likewise, if an instrument was approaching a rotational joint limit, and there was no way to initiate an instrument flip from the surgeon console, then the clinical staff would have to extract the instrument, and then re-insert, which increases the time of the procedure. The instrument flip algorithm according to the present disclosure resolves these issues and enhances the usability and efficiency of the system.

According to one embodiment of the present disclosure, a surgical robotic system includes a robotic arm having an instrument drive unit and a surgical instrument rotatable by the instrument drive unit about an instrument axis. The system also includes a surgical console including at least one handle controller having a handle rotatable about a handle axis and configured to receive a user input for moving the surgical instrument. The system further includes a controller configured to receive the user input and to instruct the robotic arm to flip the surgical instrument in response to the user input, wherein the user input is an angle of rotation of the handle about the handle axis that is less than an angle of rotation of the surgical instrument of about 180°.

According to one aspect of the above embodiment, the angle of rotation of the handle is from about 110° to about 160°. The instrument drive unit is configured to rotate the surgical instrument a plurality of revolutions from a center position until a mechanical limit is reached. The controller is further configured to determine whether a rotation of the surgical instrument in the same direction as rotation of the handle would encounter the mechanical limit. The controller is further configured to rotate the surgical instrument in an opposite direction as the rotation of the handle in response to determination of encountering the mechanical limit.

According to another aspect of the above embodiment, the controller is further configured to scale the user input of the angle of rotation of the handle to the angle of rotation of the surgical instrument. The surgical console further includes a display configured to display a user interface for selecting a threshold for angle of rotation of the handle. The controller is further configured to calculate a scaling factor to scale the user input of the angle of rotation of the handle. The surgical console further includes a foot pedal when actuated is configured to clutch the at least one handle controller to prevent the user input from moving the surgical instrument until the foot pedal is released.

According to another embodiment of the present disclosure, a surgical robotic system is disclosed. The system includes a robotic arm including an instrument drive unit and a surgical instrument coupled to the instrument drive unit and rotatable by the instrument drive unit about an instrument axis. The system also includes a surgical console having at least one handle controller having a handle rotatable about a handle axis and configured to receive a user input for moving the surgical instrument; and a foot pedal configured to clutch the at least one handle controller. The system further includes a controller configured to receive the user input and to instruct the robotic arm to flip the surgical instrument by rotating the surgical instrument 180° in response to the user input, wherein the user input includes rotating the at least one handle controller about the handle axis while the foot pedal is actuated at an angle of rotation that is less than 180°.

According to one aspect of the above embodiment, the angle of rotation of the handle is from about 110° to about 160°. The instrument drive unit is configured to rotate the surgical instrument a plurality of revolutions from a center position until a mechanical limit is reached. The controller is further configured to determine whether a rotation of the surgical instrument in the same direction as rotation of the handle would encounter the mechanical limit. The controller is further configured to rotate the surgical instrument in an opposite direction as the rotation of the handle in response to determination of encountering the mechanical limit. The controller is further configured to scale the user input of the angle of rotation of the handle to the angle of rotation of the surgical instrument. The surgical console includes a display configured to display a user interface for selecting a threshold for angle of rotation of the handle. The controller is further configured to calculate a scaling factor to scale the user input of the angle of rotation of the handle.

According to another embodiment of the present disclosure, a method for controlling a surgical robotic system is disclosed. The method includes actuating a foot pedal of a surgical console to disengage a handle controller of the surgical console from controlling a surgical instrument and rotating a handle of the handle controller about a handle rotation axis while the foot pedal is actuated at an angle of rotation that is less than 180°. The method also includes determining at a controller whether the angle of rotation exceeds a threshold angle of rotation and rotating the surgical instrument 180° about an instrument axis in response to the angle of rotation exceeding the threshold angle of rotation.

According to one aspect of the above embodiment, the threshold angle of rotation is from about 110° to about 160°. The method further includes determining whether a rotation of the surgical instrument in the same direction as rotation of the handle would encounter a mechanical limit; and rotating the surgical instrument in an opposite direction as the rotation of the handle in response to determination of encountering the mechanical limit.

BRIEF DESCRIPTION OF THE DRAWINGS

Various embodiments of the present disclosure are described herein with reference to the drawings wherein.

DETAILED DESCRIPTION

Figure 1:
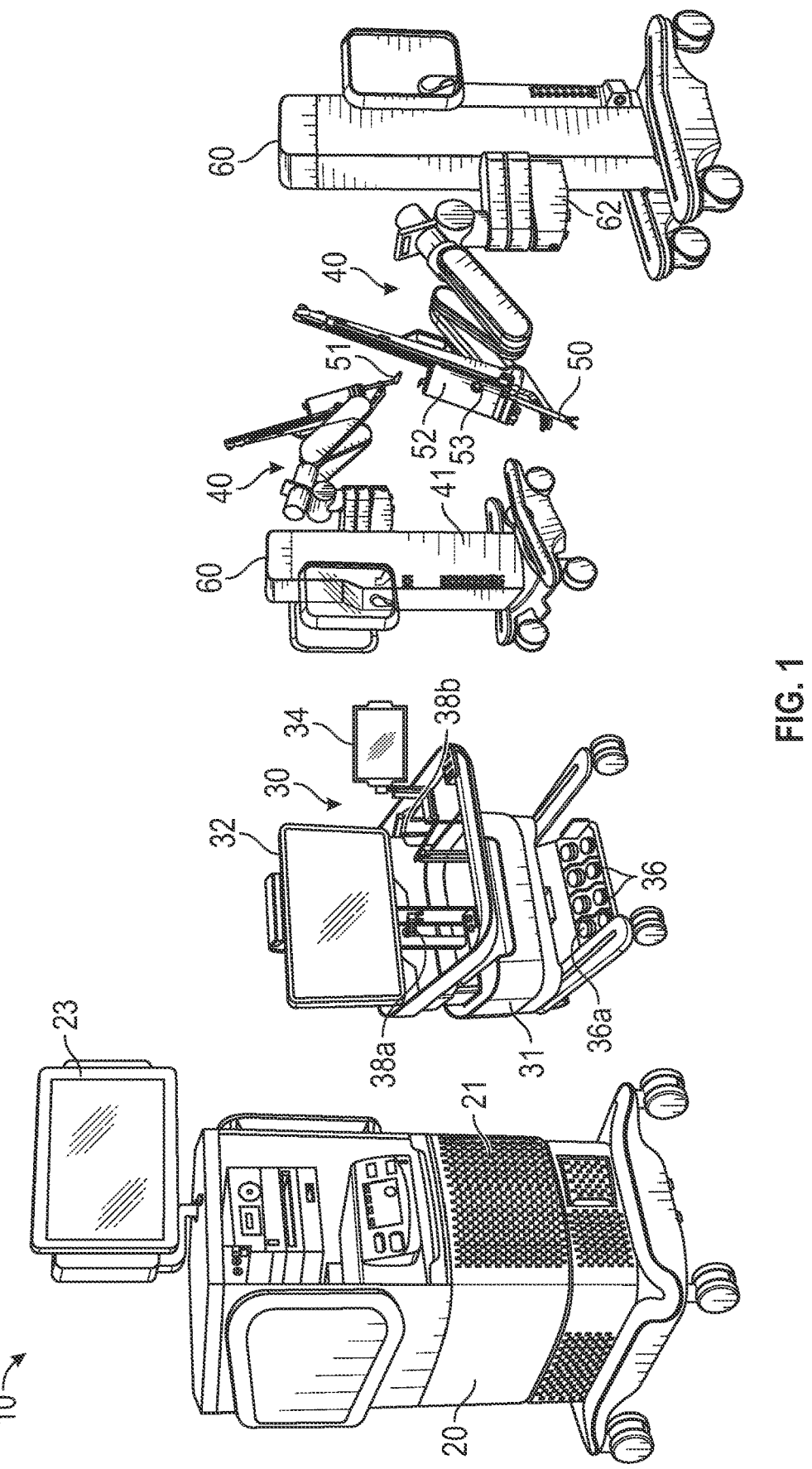
FIG. 1 is a schematic illustration of a surgical robotic system including a control tower, a console, and one or more surgical robotic arms according to an embodiment of the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, an IOT device, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscope camera 51, configured to provide a video feed for the clinician. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue whilst deploying a plurality of tissue fasteners, e.g., staples, and cutting stapled tissue.

One of the robotic arms 40 may include a camera 51 configured to capture video of the surgical site. The surgical console 30 includes a first display 32, which displays a video feed of the surgical site provided by camera 51 of the surgical instrument 50 disposed on the robotic arms 40, and a second interaction display 34, which displays a user interface for controlling the surgical robotic system 10. The first and second displays 32 and 34 are touchscreens allowing for displaying various graphical user inputs.

The surgical console 30 also includes a plurality of user interface devices, such as pedals 36 and a pair of handle controllers 38a and 38b which are used by a user to remotely control robotic arms 40. The surgical console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38a and 38b.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, nonvolatile, magnetic, optical, or electrical media, such as read-only memory (ROM), random access memory (RAM), electrically-erasable programmable ROM (EEPROM), nonvolatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
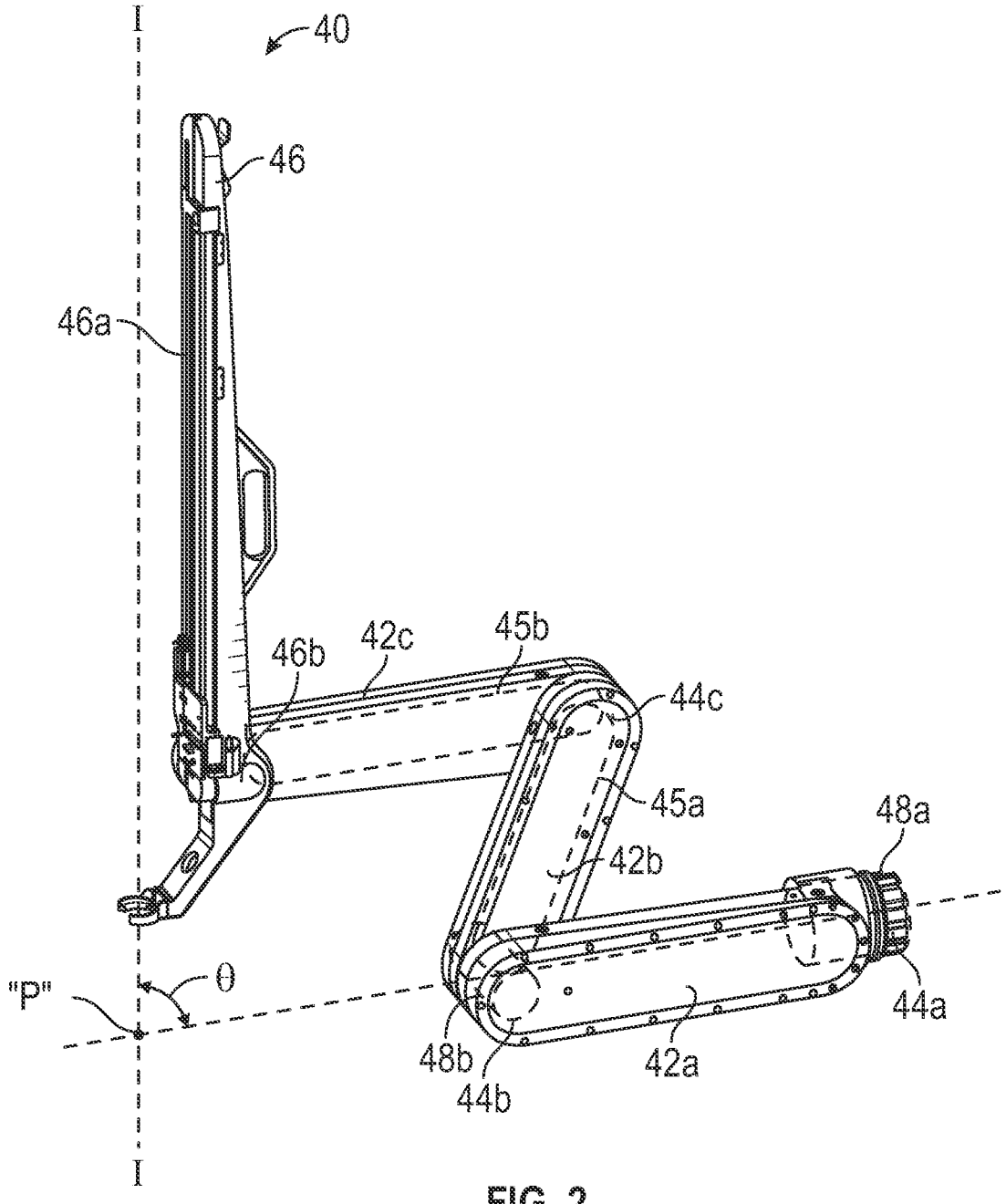
FIG. 2 is a perspective view of a surgical robotic arm of the surgical robotic system of FIG. 1 according to an embodiment of the present disclosure.
Figure 3:
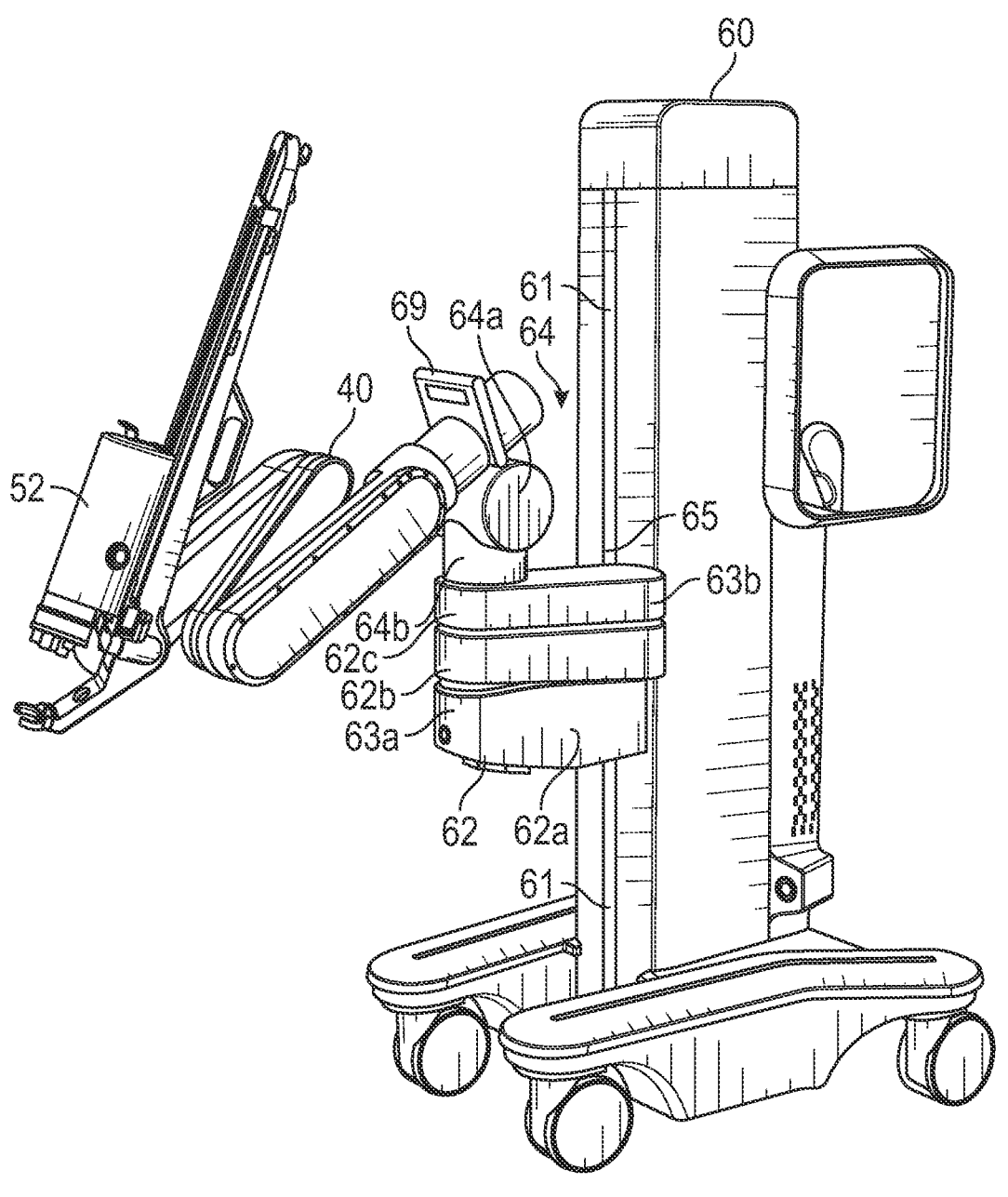
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are interconnected at joints 44a, 44b, 44c, respectively. The joint 44a is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62a, 62b, 62c as well as the lift 61.

The third link 62c includes a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

With reference to FIG. 2, the robotic arm 40 also includes a holder 46 defining a second longitudinal axis and configured to receive an IDU 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effectors) of the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c.

The robotic arm 40 also includes a plurality of manual override buttons 53 disposed on the IDU 52 and the setup arm 62, which may be used in a manual mode. The clinician may press one or more of the buttons 53 to move the component associated with the button 53.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

The actuator 48b of the joint 44b is coupled to the joint 44c via the belt 45a, and the joint 44c is in turn coupled to the joint 46c via the belt 45b. Joint 44c may include a transfer case coupling the belts 45a and 45b, such that the actuator 48b is configured to rotate each of the links 42b, 42c and the holder 46 relative to each other. More specifically, links 42b, 42c, and the holder 46 are passively coupled to the actuator 48b which enforces rotation about a remote center point "P" which lies at an intersection of the first axis defined by the link 42a and the second axis defined by the holder 46. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

Figure 4:
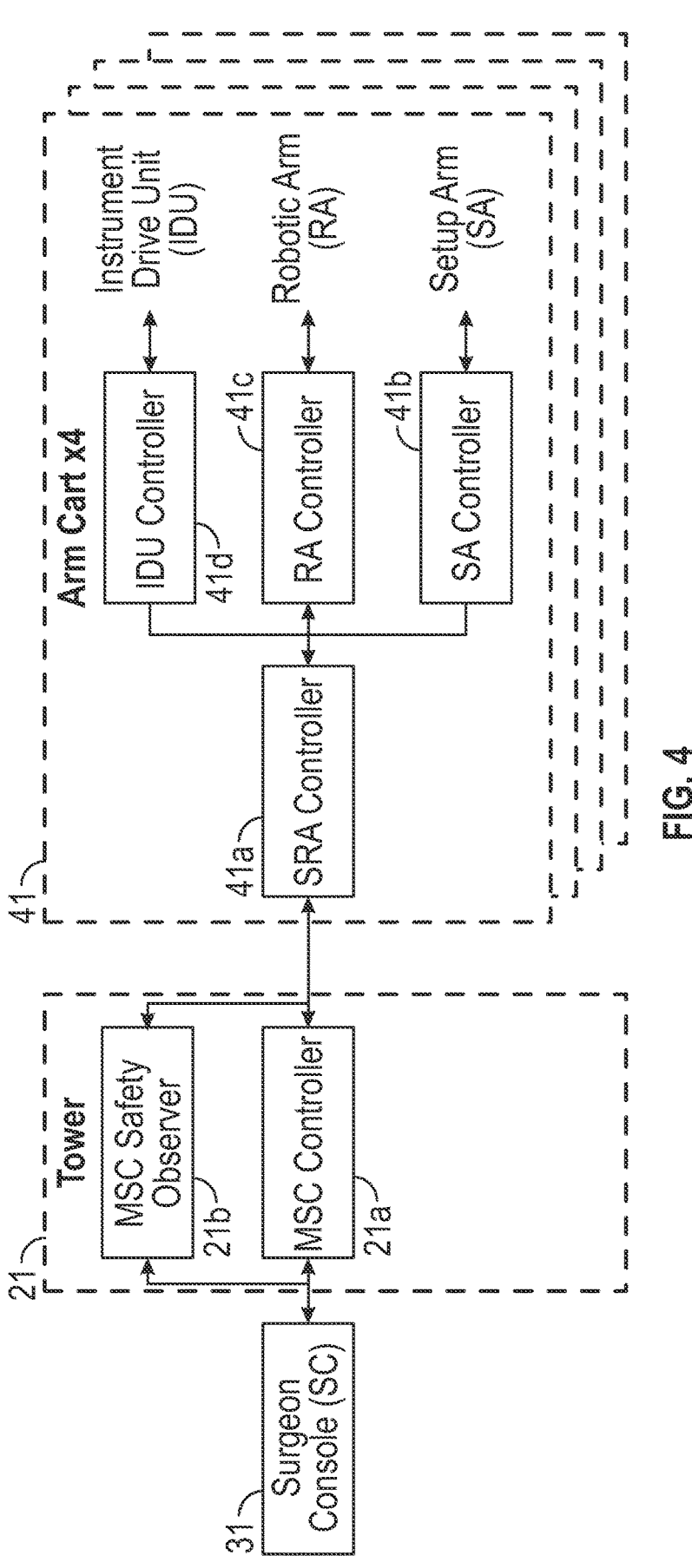
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives back the actual joint angles and uses this information to determine force feedback commands that are transmitted back to the computer 31 of the surgical console 30 to provide haptic feedback through the handle controllers 38a and 38b. The handle controllers 38a and 38b include one or more haptic feedback vibratory devices that output a haptic feedback. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled as follows. Initially, a pose of the handle controller controlling the robotic arm 40, e.g., the handle controller 38a, is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In embodiments, the coordinate position is scaled down and the orientation is scaled up by the scaling function. In addition, the controller 21a also executes a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

With reference to FIG. 1, movement of the handle controllers 38a and 38b results in the movement of the instrument 50. To simplify the description of the present disclosure only reference to the handle controller 38a is made, and the handle controller 38b may be configured to operate in a similar manner. In embodiments, one of the foot pedals 36, namely, a clutch foot pedal 36a, is configured to adjust movement input signals of the handle controller 38a. The movement of the instrument 50 and/or the robotic arm 40 is adjusted based on a predetermined scaling factor, which may be adjusted by the clutch foot pedal 36a. In embodiments, pressing the clutch foot pedal 36a halfway between a fully-open and fully-engaged position similarly scales any input from the handle controller 38a by half, such that distances traveled by the instrument 50 and the robotic arm 40 are halved. In further embodiments, pressing the clutch foot pedal 36a completely downward to the fully-engaged position keeps the robotic arm 40 and the instrument 50 stationary to allow for shifting of the handle controller 38a without moving the instrument 50 and/or the robotic arm 40.

Figure 5:
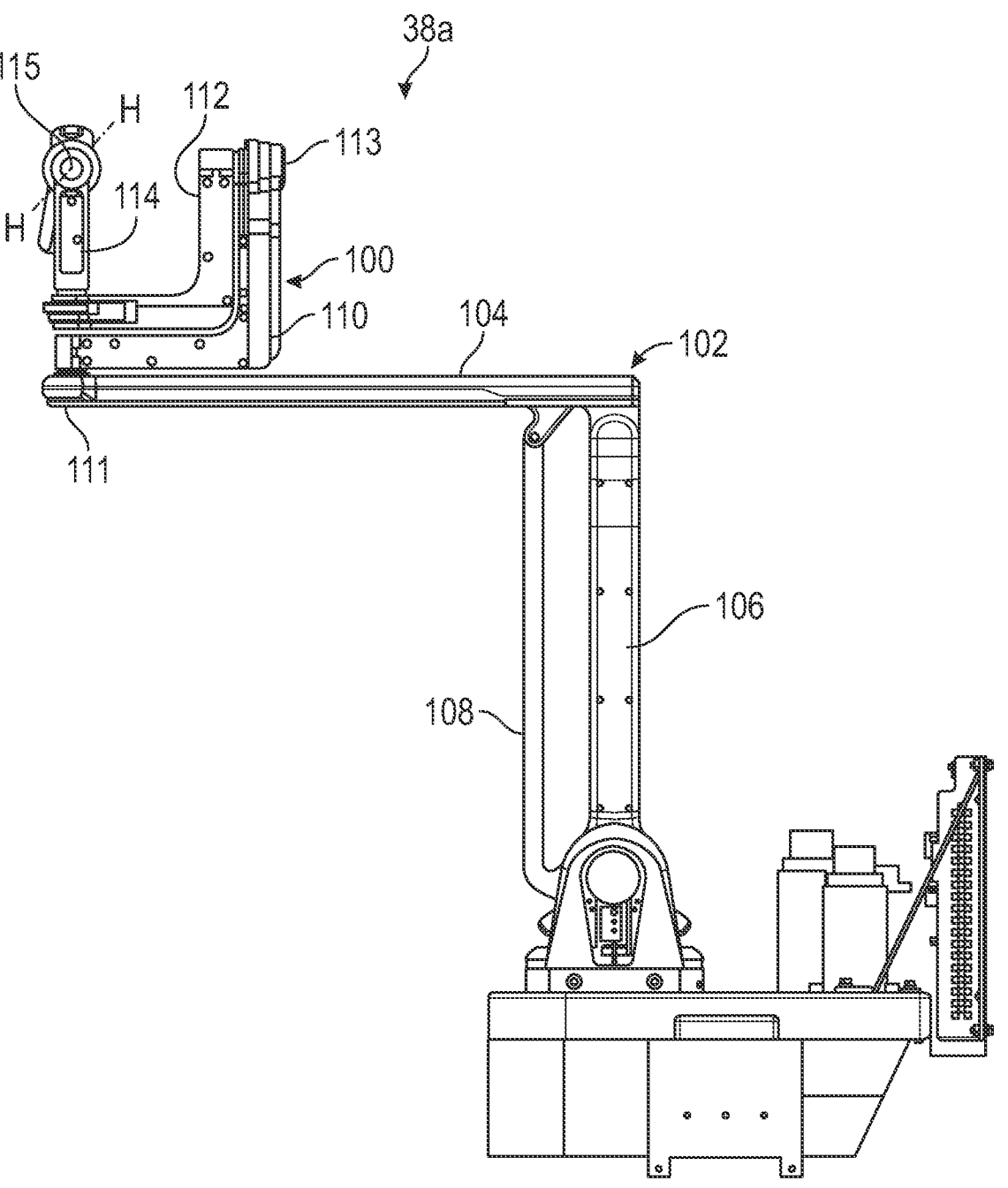
FIG. 5 is a side view of a handle controller of the surgical robotic system of FIG. 1 according to an embodiment of the present disclosure.

With reference to FIG. 5, the handle controller 38a includes a handle assembly 100 coupled to a linkage 102 having a horizontal link 104 and a pair of vertical links 106 and 108. The linkage 101 allows for inputting horizontal and vertical movement commands. The handle assembly 100 includes a first frame 110 rotationally coupled to the linkage 102 at a first gimbal 111, a second frame 112 rotationally coupled to the first frame 110 at a second gimbal 113, and a handle 114 coupled to the second frame 112 at a third gimbal 115. The handle 114 is configured to rotate about a longitudinal (i.e., roll) axis "H-H" passing through the third gimbal 115. Rotation of the handle 114 about the roll axis "H-H" imparts rotation of the instrument 50 about its longitudinal (i.e., roll) axis "I-I" (FIG. 2).

Rotation of the instrument 50 about the roll axis "I-I" is accomplished by the IDU 52, which rotates the instrument 50. The IDU 52 is configured to rotate the instrument 50 a plurality of revolutions about the roll axis "I-I" until a mechanical limit is reached. In embodiments, the instrument 50 may be rotated from a central position+/−360° to +/−1080°. As used herein, notation "+/−" followed by a degree number denotes rotation in either counterclockwise or clockwise direction by that degree amount. Thus, even though the instrument 50 may be rotated continuously during surgery for multiple revolutions, on occasion, mechanical limits are reached. The system 10, and in particular the controller 21a is configured to control the IDU 52 to rotate the instrument 50 in those situations where mechanical limits are reached by flipping the instrument 50.

In particular, the controller 21a flips the instrument 50 by instructing the IDU 52 to rotate the instrument +/−180° in the axial direction that is opposite from the mechanical limit. This feature avoids encountering mechanical hard stops on the roll axis "H-H", and thus enhances the range-of-motion. Instrument flip may be initiated when the clinician clutches the handle controller 38a via the foot pedal 36a and rotates the handle 114 about the roll axis "H-H" by any suitable angle, which may be less than an actual flip or instrument rotation angle, i.e., 180°, to allow for easier input of the movement command. The handle rotation angle may be from about 110° to about 160°, which in embodiments may be from about 120° to about 150° in either direction. In further embodiments, the handle rotation angle may be +/−135°. This allows the clinician to indicate that the instrument 50 is to be flipped, i.e., rotated 180°, without actually rotating the handle 114 by that amount. The controller 21a is configured to scale the handle rotation angle input, which is less than the instrument rotation angle, i.e., 180°, by a scaling factor to achieve the flip of the instrument 50.

In embodiments, while the instrument flip command may be in either direction, e.g., +/−135°, the actual rotation of the instrument 50 may be done in the direction of the flip as long as a mechanical limit would not be reached by the 180° rotation of the instrument. Thus, the rotation of the instrument 50 is performed in the direction of the rotation of the handle 114 unless a mechanical limit would be reached by the rotation of the instrument 50, in which case, the instrument 50 is rotated 180° in the opposite direction that allows for the rotation of the instrument 50.

During surgery, while the handle 114 may be within a comfortable working range (e.g., natural hand holding position) of the roll axis "H-H" the IDU 52 may be near a mechanical joint limit. The controller 21a allows the clinician to use the instrument flip function to redefine the working range of the IDU 52 on the handle controller 38a to a new region of the range of motion of the IDU 52. This is apparent when using curved-tip instruments, which upon insertion may be initially pointing in the opposite direction from what the clinician needs. By using the instrument flip function, the instrument 50, including the end effector, is rotated 180° to point the end effector in the desired direction. The instrument flip function initiates an instrument flip algorithm is embodied in software instructions executed by the controller 21a and handles the logic for when to apply a preset axial rotation offset and in which direction. Axial rotations are then applied to the IDU 52. In embodiments, axial rotation may not be instantaneously applied to the instrument 50 by the IDU 52 in response to the instrument flip command, but rather, the instrument 50 may be rotated to the new orientation after a brief motion of the handle 114. The instructions for carrying out the rotation are embodied in software instructions executed by main cart controller 41a.

Figure 6:
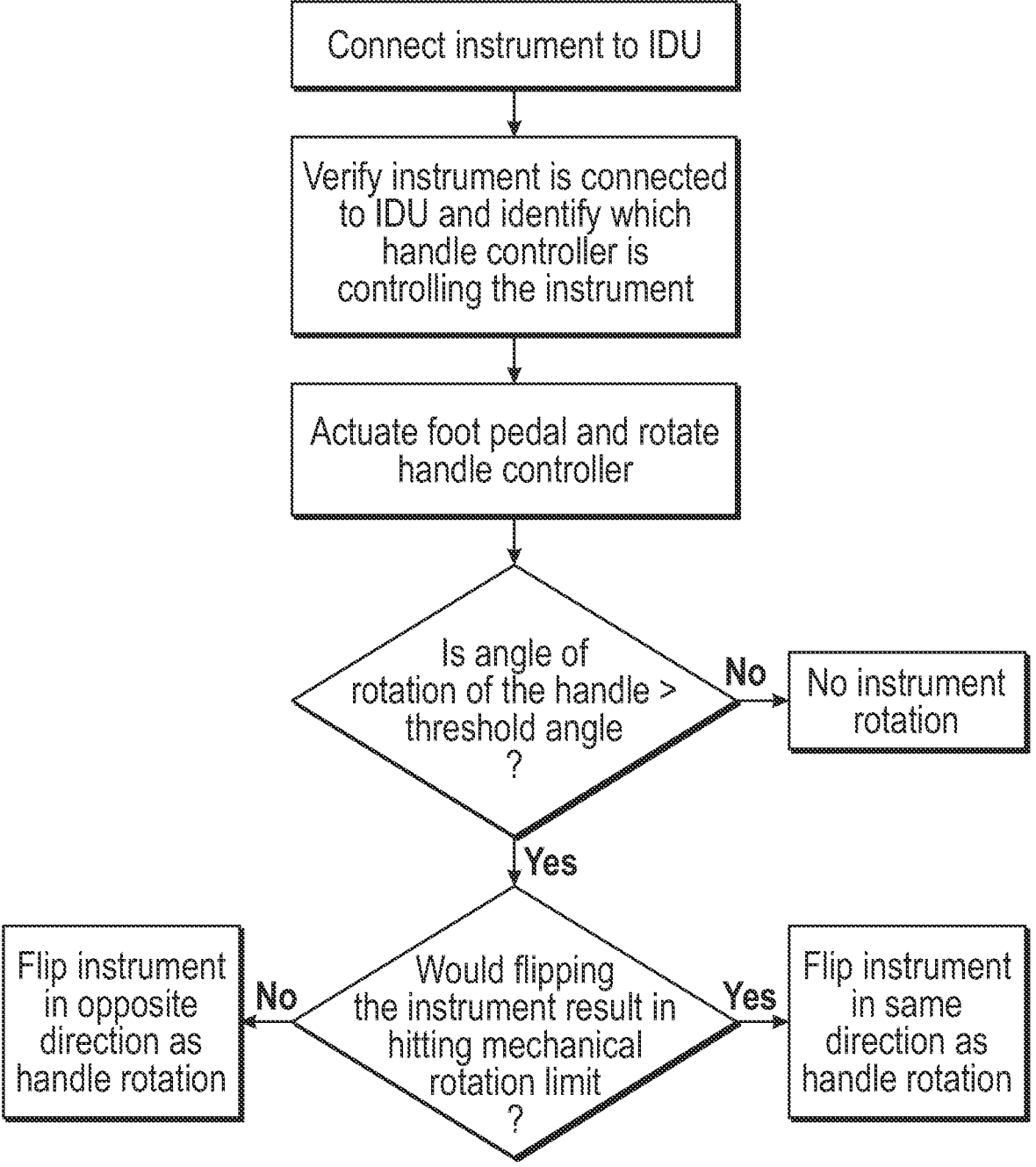
FIG. 6 is a flow chart of a method for performing an instrument flip using the handle controller of FIG. 5 according to an embodiment of the present disclosure.

With reference to FIG. 6, a method of the instruction flip algorithm initially checks to ensure that the instrument 50 is engaged to the IDU 52 and the main cart controller 41a is in communication with the instrument 50. The verification is performed by the main controller 41a. The main cart controller 41a then checks which of the handle controllers 38a or 38b is assigned to the instrument 50 being controlled.

Next, the controller 21a looks for a change in the clutch state of the clutch foot pedal 36a. In particular, the controller 21a is listening for clutch input from the clutch foot pedal 36a and the specific input command based on the movement of the handle 114 requesting an instrument flip. The input command for initiating instrument flip is rotation of the handle 114 about the roll axis "H-H" by more than the threshold angle of rotation, which may be from about 90° to about 160° in either direction, and in embodiments 135° in either direction. Based on these inputs, the controller 21a selects and outputs the instrument flip angle as +180°, −180°, or 0°. The flip angle is reset to 0° if there is no instrument 50 attached. If the angle of rotation of the handle 114 is less than the threshold angle for initiating the flip function, then the handle 114 is simply rotated without rotation of the instrument 50.

The direction of rotation of the instrument 50 is also verified by determining whether rotation in the same direction as the handle 114 would result in the IDU 52 hitting the mechanical limit. If that is the case, the IDU 52 rotates the instrument 50 in the opposite direction to achieve flipping of the instrument 50.

The scaling factor and the threshold angle for initiating the instrument flip may be adjustable. The scaling factor may be adjusted such that rotating the clutched handle controller 38a in a first direction (e.g., clockwise) past the threshold could trigger an increase in scaling, whereas rotating in the opposite direction could trigger a decrease in scaling. This adjustment may also be specific to just the instrument 50 being controlled by the handle controller 38a, such that the scaling factors are not applied to the handle controller 38b. The adjustments to scaling and the threshold angle for initiating instrument flip may be adjusted through a user interface (e.g., settings menu) displayed on the interaction display 34. The scaling factor may be set automatically by the controller 21a in response to the clinician selecting a desired threshold angle since the instrument flip is about 180°.

In embodiments, other rotational threshold may be used as commands for controlling the instrument 50. These secondary rotational thresholds may be higher than the instrument flip threshold. The secondary rotational thresholds, when engaged, may be used to automate a variety of other functions performed by the instrument 50 and the IDU 52. In embodiments, these functions include straightening and opening instrument jaws in preparation for instrument exchange, relaxing or tightening instrument cable tension depending on the direction of the handle 114 motion when clutched, and enabling or disabling endoscope roll while still engaged at the surgical console 30 with hands on the handle controllers 38a and 38b, instead of changing this setting through the interaction display 34.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
a robotic arm including an instrument drive unit and a surgical instrument coupled to the instrument drive unit and rotatable by the instrument drive unit about an instrument axis, wherein the instrument drive unit is configured to rotate the surgical instrument a plurality of revolutions from a center position until a mechanical limit is reached; and
a surgical console including at least one handle controller having a handle rotatable about a handle axis and configured to receive a user input for moving the surgical instrument; and
a controller configured to:
receive the user input and to instruct the robotic arm to change orientation of the surgical instrument by applying a 180° offset about a longitudinal axis in response to the user input, wherein the user input is an angle of rotation of the handle about the handle axis that is less than an angle of rotation of the surgical instrument of about 180°; and
determine whether a rotation of the surgical instrument in the same direction as rotation of the handle would encounter the mechanical limit.

2. The surgical robotic system according to claim 1, wherein the angle of rotation of the handle is from about 110° to about 160°.

3. The surgical robotic system according to claim 1, wherein the controller is further configured to rotate the surgical instrument in an opposite direction as the rotation of the handle in response to determination of encountering the mechanical limit.

4. The surgical robotic system according to claim 1, wherein the controller is further configured to scale the user input of the angle of rotation of the handle to the angle of rotation of the surgical instrument.

5. The surgical robotic system according to claim 4, wherein the surgical console further includes a display configured to display a user interface for selecting a threshold for angle of rotation of the handle.

6. The surgical robotic system according to claim 5, wherein the controller is further configured to calculate a scaling factor to scale the user input of the angle of rotation of the handle.

7. The surgical robotic system according to claim 1, wherein the surgical console further includes a foot pedal when actuated is configured to clutch the at least one handle controller to prevent the user input from moving the surgical instrument until the foot pedal is released.

8. A surgical robotic system comprising:
a robotic arm including an instrument drive unit and a surgical instrument coupled to the instrument drive unit and rotatable by the instrument drive unit about an instrument axis, wherein the instrument drive unit is configured to rotate the surgical instrument a plurality of revolutions from a center position until a mechanical limit is reached; and
a surgical console including:

12 at least one handle controller having a handle rotatable about a handle axis and configured to receive a user input for moving the surgical instrument; and
a foot pedal configured to clutch the at least one handle controller; and
a controller configured to:
receive the user input and to instruct the robotic arm to change orientation of the surgical instrument by applying a 180° offset about a longitudinal axis of the surgical instrument by rotating the surgical instrument 180° in response to the user input, wherein the user input includes rotating the at least one handle about the handle axis while the foot pedal is actuated at an angle of rotation that is less than 180°; and
determine whether a rotation of the surgical instrument in the same direction as rotation of the handle would encounter the mechanical limit.

9. The surgical robotic system according to claim 8, wherein the angle of rotation of the handle is from about 110° to about 160°.

10. The surgical robotic system according to claim 8, wherein the controller is further configured to rotate the surgical instrument in an opposite direction as the rotation of the handle in response to determination of encountering the mechanical limit.

11. The surgical robotic system according to claim 8, wherein the controller is further configured to scale the user input of the angle of rotation of the handle to the angle of rotation of the surgical instrument.

12. The surgical robotic system according to claim 11, wherein the surgical console includes a display configured to display a user interface for selecting a threshold for angle of rotation of the handle.

13. The surgical robotic system according to claim 12, wherein the controller is further configured to calculate a scaling factor to scale the user input of the angle of rotation of the handle.

14. A method for controlling a surgical robotic system, the method comprising:
actuating a foot pedal of a surgical console to disengage a handle controller of the surgical console from controlling a surgical instrument;
rotating a handle of the handle controller about a handle rotation axis while the foot pedal is actuated at an angle of rotation that is less than 180°; and
determining at a controller whether the angle of rotation exceeds a threshold angle of rotation;
rotating the surgical instrument 180° about an instrument axis in response to the angle of rotation exceeding the threshold angle of rotation;
determining whether a rotation of the surgical instrument in the same direction as rotation of the handle would encounter a mechanical limit; and
rotating the surgical instrument in a direction opposite the rotation of the handle in response to a determination of encountering the mechanical limit.

15. The method according to claim 14, wherein the threshold angle of rotation is from about 110° to about 160°.

* * * * *